(12) United States Patent
Church et al.

(10) Patent No.: US 10,842,394 B2
(45) Date of Patent: Nov. 24, 2020

(54) IN-CANAL HEART RATE MONITORING APPARATUS

(71) Applicant: Fitbit, Inc., San Francisco, CA (US)

(72) Inventors: Andrew R. Church, Oakland, CA (US); Jaclyn Leverett Wasson, Berkeley, CA (US); Daniel Joel Freschl, Berkeley, CA (US); Esther Vigil-Ruiz, Sebastopol, CA (US)

(73) Assignee: Fitbit, Inc., San Francisco, CA (US)

( * ) Notice: Subject to any disclaimer, the term of this patent is extended or adjusted under 35 U.S.C. 154(b) by 114 days.

(21) Appl. No.: 15/900,612

(22) Filed: Feb. 20, 2018

(65) Prior Publication Data

US 2018/0177416 A1    Jun. 28, 2018

Related U.S. Application Data

(63) Continuation-in-part of application No. 15/582,240, filed on Apr. 28, 2017, now Pat. No. 10,433,739.

(60) Provisional application No. 62/329,861, filed on Apr. 29, 2016, provisional application No. 62/460,421, filed on Feb. 17, 2017, provisional application No. 62/460,544, filed on Feb. 17, 2017.

(51) Int. Cl.
*A61B 5/024* (2006.01)
*A61B 5/00* (2006.01)

(52) U.S. Cl.
CPC ...... *A61B 5/02433* (2013.01); *A61B 5/02438* (2013.01); *A61B 5/681* (2013.01); *A61B 5/6814* (2013.01); *A61B 5/6815* (2013.01); *A61B 5/7207* (2013.01); *A61B 5/7221* (2013.01)

(58) Field of Classification Search
CPC .......... A61B 5/02416–02444; A61B 5/14551–14552; A61B 5/6814–6817; A61B 5/6824; A61B 5/6831; A61B 5/681
See application file for complete search history.

(56) References Cited

U.S. PATENT DOCUMENTS

| | | | |
|---|---|---|---|
| 8,886,269 B2 | 11/2014 | LeBoeuf et al. | |
| 8,923,941 B2 | 12/2014 | LeBoeuf et al. | |
| 8,929,965 B2 | 1/2015 | LeBoeuf et al. | |
| 8,989,830 B2 | 3/2015 | LeBoeuf et al. | |
| 2005/0209516 A1* | 9/2005 | Fraden | A61B 5/02055 600/323 |
| 2010/0217102 A1* | 8/2010 | LeBoeuf | A61B 5/4812 600/310 |
| 2014/0180158 A1* | 6/2014 | Cheng | A61B 5/6803 600/544 |

(Continued)

*Primary Examiner* — Thaddeus B Cox
(74) *Attorney, Agent, or Firm* — Hogan Lovells US LLP

(57) ABSTRACT

A wearable computing device includes one or more processors, memory and a physiological metric sensor system, including a light source configured to direct light into tissue of a user wearing the wearable computing device, a light detector implemented a distance away from the light source and configured to detect light from the light source that reflects back from the user, and a light-blocking portion implemented between the light source and the light detector. The wearable computing device may further include an audio port directed towards an ear canal of the user and control circuitry configured to activate the light source during a period of time and generate a light detector signal indicating an amount of light detected by the light detector during the period of time.

20 Claims, 6 Drawing Sheets

(56) References Cited

U.S. PATENT DOCUMENTS

| | | | |
|---|---|---|---|
| 2015/0351688 A1* | 12/2015 | Just | A61B 5/681 |
| | | | 600/407 |
| 2016/0287108 A1* | 10/2016 | Wei | A61B 5/02427 |
| 2017/0118551 A1* | 4/2017 | Wagner | A61B 5/6802 |
| 2017/0120107 A1* | 5/2017 | Wisbey | G09B 19/00 |
| 2017/0150919 A1* | 6/2017 | Chuang | A61B 5/0002 |
| 2018/0020960 A1* | 1/2018 | Sarussi | G01N 33/492 |
| | | | 600/310 |
| 2018/0020979 A1* | 1/2018 | Wagner | A61B 5/14552 |
| | | | 600/379 |

* cited by examiner

IN-CANAL HEART RATE MONITORING APPARATUS

CROSS-REFERENCE TO RELATED APPLICATION

This application is a continuation-in-part and claims priority to U.S. application Ser. No. 15/582,240 filed Apr. 28, 2017, now U.S. Pat. No. 10,433,739, entitled MULTI-CHANNEL PHOTOPLETHYSMOGRAPHY SENSOR, which claims priority to U.S. Provisional Application No. 62/329,861 filed Apr. 29, 2016, entitled MULTI-CHANNEL PHOTOPLETHYSMOGRAPHY SENSOR, the disclosure of each of which is expressly incorporated by reference herein in its entirety. This application claims priority to U.S. Provisional Application No. 62/460,421 filed Feb. 17, 2017, entitled IN-CANAL HEART RATE MONITORING APPARATUS, the disclosure of which is expressly incorporated by reference herein in its entirety. This application also claims priority to U.S. Provisional Application No. 62/460,544 filed Feb. 17, 2017, entitled PPG SENSOR WITH LIGHT FIELD MANAGEMENT FEATURES, the disclosure of which is expressly incorporated by reference herein in its entirety.

TECHNICAL FIELD

This disclosure relates to the field of wearable devices, and particularly to techniques for using photoplethysmography (PPG) sensors to generate heart rate (HR) and other physiological metrics.

BACKGROUND

A PPG sensor may be utilized to detect the volumetric change in blood vessels. A PPG sensor usually includes a light source, typically a light-emitting diode (LED), and a light-sensitive sensor, such as a photodiode. Blood passing through the vasculature between the light source and the sensor will modulate the light path between the two, resulting in a deviation in the current produced by the photodiode. By applying various algorithms to the signal sensed by the photodiode, an HR estimate can be determined.

PPG technologies may rely on emitting wavelengths of green, red, and/or infrared (IR) light from an LED. Many wearable PPG devices use green light, as the hemoglobin absorption of light can be up to 20 times greater at green wavelengths than at IR wavelengths. Additionally, in some cases, green LED light sources may provide superior results in terms of cost, form factor, and power efficiency.

SUMMARY

In some implementations, the present disclosure relates to a wearable computing device comprising one or more processors, memory, and a physiological metric sensor system, including a light source configured to direct light into tissue of a user wearing the wearable computing device, a light detector implemented a distance away from the light source and configured to detect light from the light source that reflects back from the user and a light-blocking portion implemented between the light source and the light detector. The wearable computing device may further include an audio port directed towards an ear canal of the user and control circuitry configured to activate the light source during a period of time and generate a light detector signal indicating an amount of light detected by the light detector during the period of time.

In some embodiments, the wearable computing device further comprises one or more light field management features configured to steer or direct light from the light source to the light detector. In some embodiments, the one or more light field management features include at least one of a prism, light pipe, total internal reflection mirror, metallized mirror and a diffractive optical element.

In some embodiments, the physiological metric sensor system is physically coupled to the audio port. In some embodiments, the physiological metric sensor system includes a photoplethysmographic (PPG) sensor, the PPG sensor including the light source and the light detector. In some embodiments, the light source is a light-emitting diode (LED) and the light detector is a photodiode.

In some embodiments, the light source and the light detector are implemented on an outer surface of the audio port, the outer surface substantially perpendicular to a direction in which sound from the audio port is projected.

In some embodiments, the light source and the light detector are implemented on an outer surface of the audio port, to provide that a configuration of the audio port in the ear canal of the user to optimize sound quality corresponds to a configuration of the light source and light detector to optimize light field management.

In some embodiments, the wearable computing device further comprises an audio tip coupled to the audio port, the audio tip comprising an optically transparent portion and comprising the light-blocking portion implemented between the light source and the light detector. In some embodiments, the audio tip has a first size of a set of sizes. In some embodiments, the light-blocking portion is opaque and in some embodiments, the audio tip is made of silicone gel.

In some embodiments, the light-blocking portion includes a light-blocking rib extending in a radial direction from the axis of the audio port to the optically transparent portion of the audio tip. In some embodiments, the light-blocking portion has a light source window to facilitate emission of light and a light detector window to facilitate detection of light.

In some embodiments, the distance away from the light source corresponds to an angle between the light source and the light detector such that the amount of light travels a threshold distance in the tissue of the user and the amount of light meets a threshold percentage of light generated by the light source.

In some embodiments, the audio port is communicatively coupled to an audio source. In some embodiments, the control circuitry is further configured to determine a physiological metric value based on the light detector signal. In some embodiments, the physiological metric sensor system includes a second light source and in some embodiments, the physiological metric sensor system includes a second light detector.

In some implementations, the present disclosure relates to a method of providing a wearable computing device. The method comprises providing an outer housing of the wearable computing device, implementing an audio port by coupling it to the outer housing of the wearable computing device and implementing a light source configured to direct light into tissue of a user wearing the wearable computing device, on an outer surface of the audio port. The method includes implementing a light detector on the outer surface of the audio port a distance away from the light source, the light detector configured to detect light from the light source that reflects back from the user and implementing a light-blocking portion between the light source and the light detector.

In some implementations, the method further comprises implementing one or more light field management features proximal to one or both of the light source and the light detector. In some embodiments, the outer surface of the audio port is substantially perpendicular to a direction in which sound from the audio port is projected.

In some implementations, the method further comprises implementing the light source and the light detector to provide that a configuration of the audio port in an ear canal of the user to optimize sound quality corresponds to a configuration of the light source and light detector to optimize light field management.

In some implementations, the method further comprises coupling an audio tip to the audio port, the audio tip comprising an optically transparent portion and comprising the light-blocking portion implemented between the light source and the light detector.

In some implementations, implementing the light-blocking portion includes providing a light-blocking rib extending in a radial direction from an outer surface of the audio port to the optically transparent portion of the audio tip. In some implementations, implementing the light-blocking portion includes providing a light source window to facilitate emission of light and providing a light detector window to facilitate detection of light.

In some implementations, implementing a light detector on the outer surface of the audio port a distance away from the light source includes providing an angle between the light source and the light detector such that an amount of light emitted by the light source travels a threshold distance in the tissue of the user and an amount of light detected by the light detector meets a threshold percentage of the amount of light emitted by the light source.

In some implementations, the present disclosure relates to a system for determining values of physiological metrics comprising a physiological metric sensor system of a wearable computing device, including a light source configured to direct light into tissue of a user wearing the wearable computing device, a light detector implemented a distance away from the light source and configured to detect light from the light source that reflects back from the user and a light-blocking portion implemented between the light source and the light detector. The system may further include a client computing device communicatively coupled to the wearable computing device and configured to receive data related to detected light readings at the light detector.

In some embodiments, the client computing device is further configured to determine the values of the physiological metrics based on the received data related to detected light readings at the light detector. In some embodiments, the system further comprises control circuitry of the wearable computing device, the control circuitry configured to determine the values of the physiological metrics based on the detected light readings at the light detector.

In some embodiments, the system further comprises a server system, the server system configured to receive data related to detected light readings at the light detector. In some embodiments, the server system is further configured to associate the received data related to detected light readings at the light detector, with a profile of the user.

In some embodiments, the client computing device comprises an electronic display and is further configured to display information corresponding to the detected light readings at the light detector, on the electronic display.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
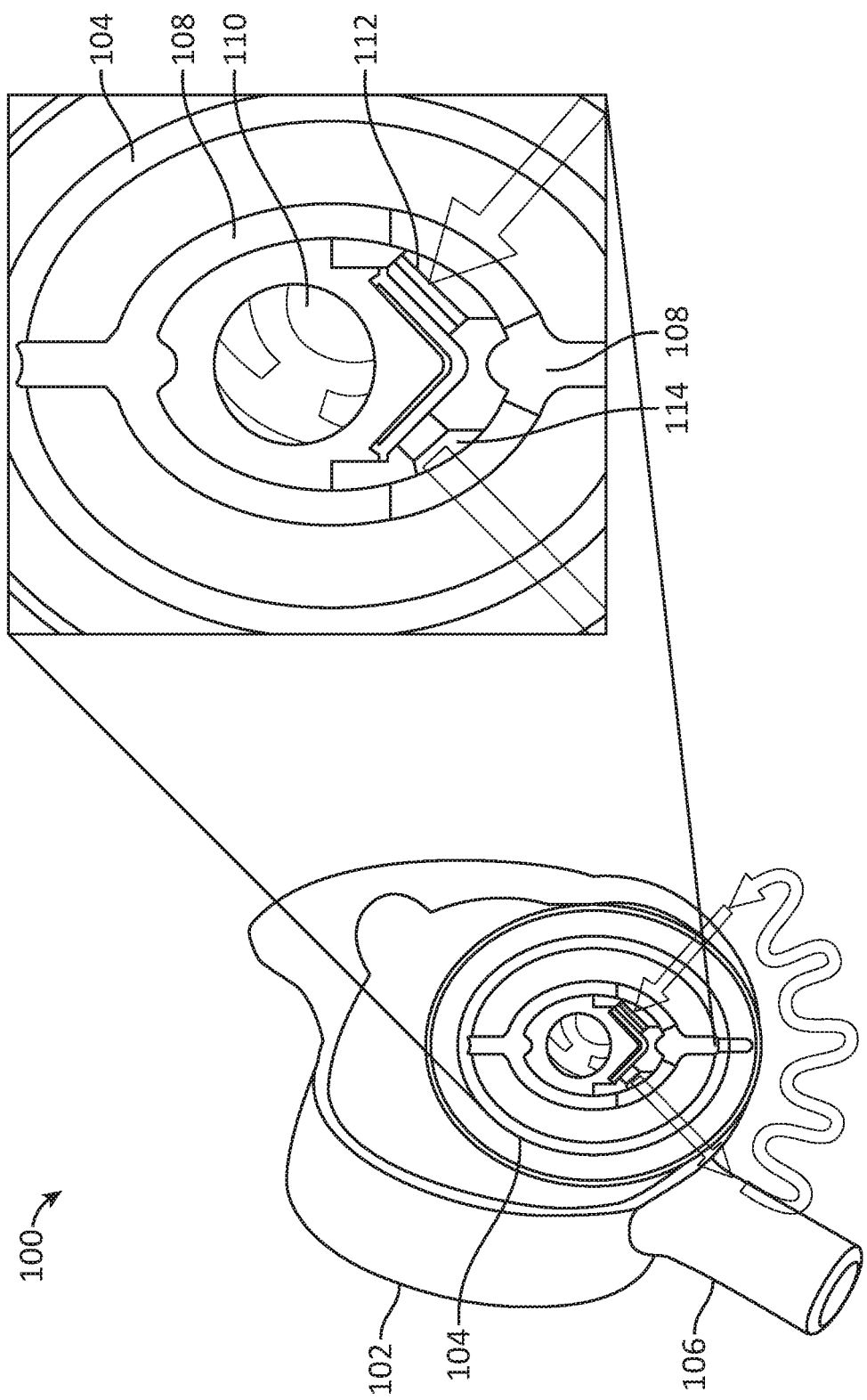
FIG. 1 illustrates a cross-sectional view of an example in-ear heart rate monitoring device in accordance with aspects of this disclosure.

The headings provided herein are for convenience only and do not necessarily affect the scope or meaning of the claimed invention. Like reference numbers and designations in the various drawings may or may not indicate like elements.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Biometric Monitoring

In some implementations, the present disclosure is related to biometric monitoring devices. The term "biometric monitoring device" is used herein according to its broad and ordinary meaning, and may be used in various contexts herein to refer to any type of biometric tracking devices, personal health monitoring devices, portable monitoring devices, portable biometric monitoring devices, or the like. In some embodiments, biometric monitoring devices in accordance with the present disclosure may be wearable devices, such as may be designed to be worn (e.g., continuously) by a person (i.e., "user," "wearer," etc.). When worn, such biometric monitoring devices may be configured to gather data regarding activities performed by the wearer, or regarding the wearer's physiological state. Such data may include data representative of the ambient environment around the wearer or the wearer's interaction with the environment. For example, the data may comprise motion data regarding the wearer's movements, ambient light, ambient noise, air quality, etc., and/or physiological data obtained by measuring various physiological characteristics of the wearer, such as heart rate, perspiration levels, and the like.

In some cases, a biometric monitoring device may leverage other devices external to the biometric monitoring device, such as an external heart rate monitor in the form of an EKG sensor for obtaining heart rate data, or a GPS receiver in a smartphone may be used to obtain position data, for example. In such cases, the biometric monitoring device may communicate with these external devices using wired or wireless communications connections. The concepts disclosed and discussed herein may be applied to both stand-alone biometric monitoring devices as well as biometric monitoring devices that leverage sensors or functionality provided in external devices, e.g., external sensors, sensors or functionality provided by smartphones, etc.

Biometric Monitoring Devices

Systems, devices and/or methods/processes in accordance with the present disclosure may comprise, or be implemented in connection with, a biometric monitoring device. Embodiments of the present disclosure may provide biometric monitoring devices configured to determine values of one or more physiological metric (e.g., heart rate) using information derived from one or more physiological metric sensors associated with an audio port of the biometric monitoring device. It is to be understood that while the concepts and discussion included herein are presented in the context of biometric monitoring devices, these concepts may also be applied in other contexts as well if the appropriate hardware is available. For example, some or all of the relevant sensor functionality or processing may be incorporated in one or more external computing devices (e.g., smartphone) communicatively coupled to the biometric monitoring device.

Physiological Metric Sensor Module

An optical physiological metric sensor such as photoplethysmography (PPG) sensors may generally utilize light sensors and/or detectors to obtain a volumetric measurement relating to pulsatile blood flow in the body. PPG information may be obtained illuminating the skin of a subject and measuring changes in light absorption. A PPG sensor can be designed to monitor the perfusion of blood to the dermis and/or subcutaneous tissue of the skin. PPG data may be determined using a wrist-worn biometric monitoring device based on the pumping of blood to the periphery during each cardiac cycle. While the pressure pulse may be somewhat damped by the time it reaches the skin, it may nevertheless be enough to distend the arteries and/or arterioles in the subcutaneous tissue of the wearer of the biometric monitoring device. The change in volume caused by the pressure pulse may be detected by illuminating the skin with the light from one or more light source (e.g., light-emitting diodes (LEDs)) and then measuring the amount of light either transmitted or reflected to one or more light sensors (e.g., photodiode(s)). In certain embodiments, as blood flow to the skin can be modulated by various other physiological systems, the PPG sensor may further be used to monitor breathing, hypovolemia, and/or other circulatory conditions.

PPG readings can be used to determine heart rate, SpO2, and the like. While PPGs can be obtained in certain systems using transmissive absorption, with respect certain wrist-worn biometric monitoring devices disclosed herein, PPG information may be obtained using reflective absorption. For PPG signals, the DC component of the signal may be attributable to the bulk absorption of the skin tissue, while the AC component may be attributable to variation in blood volume in the skin caused by the pressure pulse of the cardiac cycle. Generally, the height of the AC component of the PPG signal may be proportional to the pulse pressure, which is the difference between the systolic and diastolic pressure in the arteries. Although certain embodiments are presented herein in the context of PPG sensors, it should be understood that ambient light data for electronic display brightness level management in accordance with the present disclosure may incorporate ambient light signals from any suitable or desirable physiological metric sensor.

Various circuits and concepts related to heart rate measurement using a PPG sensor are discussed in more detail in U.S. Provisional Patent Application No. 61/946,439, filed Feb. 28, 2014 which is hereby incorporated by reference with respect to content directed at heart rate measurements with a PPG sensor and at circuits, methods, and systems for performing such measurements.

Photoplethysmography (PPG) sensors can provide an effective method for measuring a user's heart rate (HR). As noted above, a PPG sensor may include a light source, such as an LED, and a light-sensitive sensor, such as a photodiode. Using the photodiode, a PPG device including such a PPG sensor can obtain PPG signals indicative of how the blood is passing through the vessels and generate HR estimates based on the PPG signals. As used herein, the term "PPG device," in addition to having its ordinary meaning, may refer to a device including one or more PPG sensors. For example, the PPG device may be an earbud or a headphone having a PPG sensor for measuring HR and other physiological metrics inside the ear canal.

A PPG device, such as device 100 shown in FIG. 1, may employ a single light source (e.g., light source 114) coupled to a single detector (e.g. light detector 112) (i.e., a single light path). Alternatively, a PPG device 100 may employ multiple light sources associated with a single detector or multiple detectors (i.e., two or more light paths). In other embodiments, a PPG device 100 may employ multiple detectors coupled to a single light source or multiple light sources (i.e., two or more light paths). In embodiments employing multiple light paths, the PPG device 100 may determine an average of the signals resulting from the multiple light paths before determining an HR estimate and/or other physiological metrics. As used herein, the term "light path," in addition to having its broad and ordinary meaning, may refer to the probabilistic path of photons from one location to another, such as from a light source (or emitter) to a light detector (or sensor). Photons emitted by the light emitter may follow many different paths to a given light detector. For simplicity and clarity, an approximate path of light from a given source to a given detector may be referred to as a "light path."

In some cases, if a user wearing a PPG device 100 is performing an activity involving motion (or contorting of the wrist, for example, for a wrist-worn PPG device, thereby affecting the dynamics of the blood flow within the wrist), the accuracy of the HR estimate provided by the PPG device 100 may be reduced or compromised. The light intensity received by the light detector(s) 112 may be modulated by these movements, such as at an order of magnitude greater than the desired cardiac signal. Therefore, a preprocessing step where the signal effect of these movements is removed may be desirable to improve HR estimation accuracy during user motion.

In addition to the deleterious effects of motion, other causes of reduced signal quality in PPG devices 100 may include, for example, the characteristics of the local area being sensed (e.g., presence of foreign objects such as hair, presence of blood vessels underneath, etc.), the amount of ambient light present, and/or other causes. For instance, signal quality can vary significantly as the PPG sensor (e.g., light source 114 and light detector 112) is moved, possibly even by only a few millimeters, in the area being sensed (e.g., the user's wrist, ear, etc.).

Overview of In-Canal Heart Rate Monitoring Device

The in-canal heart rate monitoring solution of the present disclosure uses a custom green LED/photodiode combination (referred to collectively as a PPG sensor). The PPG sensor is located on the audio port 110 of an audio device (e.g., PPG device 100). The LED (e.g., light source 114) and photodiode (e.g., light detector 112) may be oriented at approximately 90° to each other along the axis of the audio port 110. This angle increases emitter-sensor separation. When the audio device 100 is worn by the user, the PPG sensor (e.g., light source 114 and light detector 112) is positioned at (or near) the horizon of the first bend in the ear canal. The LED (e.g., light source 114) emits green light that is modulated by the blood flow underneath the skin of the user's ear canal and returned to the photodiode (e.g., light detector 112). Heart rate is inferred from this modulation.

In some implementations, the present disclosure relates to in-canal hart rate monitoring solutions incorporated in ear-worn PPG devices 100. In-canal heart rate monitoring solutions according to various embodiments of the present disclosure may utilize a PPG sensor having light field management features. In certain embodiments, the PPG sensor includes a combination of one or more light sources 114 (e.g., green LEDs) and one or more light detectors 112 (e.g., photodiodes) in a single package. However, it should be understood that light field management features as disclosed herein may be implemented in connection with light sources 114 and/or light detectors 112 having any suitable or desirable types and/or configurations. In certain embodiments, the light source(s) 114 may emit green light that is modulated by the blood flow underneath the skin of the user's ear canal and returned to the light detector(s) 112. Heart rate may be inferred from this modulation.

In certain embodiments, the light source(s) 114 and light detector(s) 112 of a PPG device 100 (e.g., custom LED/ photodiode combination package) are integrated with one or more light field management features (e.g., prisms, light pipes, total internal reflection mirrors, metallized mirrors, diffractive optical elements, to name a few examples), as well as one or more light blocking elements (e.g., light blocking inner ear tip 108). In connection with certain embodiments disclosed herein, the collective light emitter (e.g., light source 114) and/or light detector devices/components 112 of a PPG device 100 may be referred to as an "optical sensor assembly" of a PPG device 100, or as a "PPG sensor package," or simply "PPG sensor." In connection with certain embodiments disclosed here, the terms "optical sensor assembly" and "PPG sensor package" may be used substantially interchangeably. In certain embodiments, the optical sensor assembly of a PPG device 100 may comprise a custom package including one or more LED light sources (e.g., light source 114) and one or more photodiodes (e.g., light detector 112) combined in a single package. The optical sensor assembly of PPG devices 100 in accordance with the present disclosure may further include one or more back reflector(s) disposed behind or around the light source device 114 (e.g., LED die), which may serve to at least partially collimate the light before further directing the light using light field management features as described herein. In some implementations, a PPG device 100 comprises one or more light field management elements configured to steer or direct the emitted and/or collected light, such that the effective distance between the emitter and the detector components is effectively increased. The terms "light field management," "light field management feature," "light field management element," and the like, are used herein according to their broad and ordinary meanings, and may generally refer to optical elements, components and/or features configured to steer, direct, channel, or otherwise alter light paths or characteristics, such as with respect to either or both of angular distribution and spatial distribution, for example. Light field management features and elements in accordance with embodiments of the present disclosure may further provide light-directing functionality without substantial loss of optical power.

In some embodiments, the PPG sensor design is combined with specially designed silicone audio tips (e.g., outer ear tip 104). The audio tips may combine an optically transparent layer portion (e.g., outer ear tip 104) with an opaque, light-blocking inner portion (e.g., light blocking inner ear tip 108). This opaque, light-blocking portion may serve to mitigate direct light path (DLP) issues (which may be more pronounced due to the placement of transparent silicone materials between the audio port and the user's skin) and may ensure that the light from the emitter (e.g., light source 114) is modulated through the skin of the ear canal rather than traveling directly to the photodiode (e.g., light detector 112) without going through the skin of the ear canal.

Advantages of the in-canal heart rate monitoring device described herein may include one or more of the following: (i) the PPG signal measured from inside the ear canal can be relatively stronger (e.g., stronger cardiac component) and/or be associated with less noise than PPG signals measured from elsewhere in the ear or on the wrist; (ii) the measured signal may be less susceptible to user movement (compared to on-wrist devices, which may undergo significant user motion from the user moving his or her arms); (iii) ambient light may generally be less likely to affect the measurement of HR or other physiological metrics (compared to in-ear devices that are positioned outside the ear canal, as light may generally traverse cartilage more easily); (iv) improved reliability and/or accuracy of the measurement of HR and/or other physiological metrics; (v) light field management element(s) in accordance with the present disclosure may allow the associated optical sensor assembly (e.g., PPG sensor package) to be relatively smaller (e.g., miniaturized) and/or fitted into relatively small spaces (e.g., inside the ear canal); (vi) light field management element(s) in accordance with the present disclosure may allow for the area from which reflected light is collected to be increased without requiring the light detector(s) 112 to be disposed undesirably far away from the light source(s) 114; (vii) light field management element(s) in accordance with the present disclosure may allow detected and/or transmitted light to be shaped and/or focused to increase the signal strength of the light; and (viii) light field management element(s) (e.g., prism lenses) provided on top of the optical sensor assembly (e.g., PPG sensor package) may serve as a protection layer for the electronic components in the optical sensor assembly and may also improve water sealing and/or reliability characteristics.

Cross-Sectional View of PPG Device

FIG. 1 shows a cross-sectional view of the PPG device 100 according to an example embodiment. Here, the PPG device 100 comprises an earbud having an audio port 110, where the audio port 110 houses a PPG sensor package (e.g., a light source 114 and a light detector 112) inside the outer housing 102 of the audio port 110. In some embodiments the PPG device 100 has a PPG sensor (e.g., a light source 114 and a light detector 112) on the outer surface of the audio port 110. The illustrated cross-section is perpendicular to the axis of the ear canal, and the cross-sectional view is illustrated as if the viewer is inside the ear canal looking out of the ear canal when the PPG device 100 is worn.

As shown in FIG. 1, the light source 114 (e.g., emitter) and the light detector 112 (e.g., photodiode) are facing away from each other at about a 90 degree angle. By angling the light source 114 and the light detector 112 away from each other, the PPG devices causes the light emitted by the light source 114 to travel a greater distance underneath the skin of the ear canal before the light is received by the light detector 112, thereby increasing the amount of modulation that the light undergoes and causing the sensor data generated by the light detector 112 to have a more significant pulse or cardiac component. The angle between the light source 114 surface on which the light source 114 is mounted and the detector surface on which the light detector 112 is mounted may be less than 90 degrees (e.g., 30, 45, 60, etc.) or greater than 90 degrees (e.g., 120, 135, 150, etc.). However, the angle is not limited to a particular value and may take on any value to optimize or improve PPG sensor performance.

As shown in FIG. 1, in certain embodiments, the light source 114 and the light detector 112 are provided on the same plane (e.g., in the PPG sensor package, such as a custom LED/photodiode combination package), which may provide certain advantages from a manufacturing standpoint. The light emitted from the light source 114 component may be directed based on the characteristics of, for example, a prism, or other light field management element(s) associated with, or covering, the light source(s) 114 (e.g., the left light field management element (e.g., prism) in FIG. 1; also referred to herein as the emitter light field management element), and the light reflected towards the light detector(s) 112 may be directed based on the characteristics of, for example, a prism or other light field management element(s) associated with, or covering, the light detector(s) (shown as the right light field management element (e.g., prism) in FIG. 1; also referred to herein as the detector light field management element). By causing the light emitted from the light source(s) 114 to be angled away from the light detector(s) 112, and by causing the light reflected towards the light detector(s) 112 to be angled towards the light detector(s) 112, the light field management elements of the PPG device may cause the light emitted by the light source(s) 114 to travel a greater distance underneath the skin of the ear canal before the light is received by the light detector(s) 112, thereby increasing the amount of modulation that the light undergoes and causing the sensor data generated by the light detector(s) 112 to have a more significant pulse or cardiac component.

In certain embodiments, the PPG device of FIG. 1 further includes a light-blocking element designed to prevent the light emitted by the light source(s) 114 from going directly to the light detector(s) 112 (e.g., photodiode(s)) without traveling underneath the skin of the ear canal. The light-blocking element may extend from the surface on which the light source(s) 114 and the light detector(s) 112 are disposed to the skin of the ear canal when the PPG device 100 is worn. In other embodiments, the light-blocking element extends from the surface on which the light source(s) 114 and the light detector(s) 112 are disposed to an optically-transparent portion of the material 104 (e.g., silicone gel) disposed between the light field management elements (e.g., prisms) and the skin of the ear canal when the PPG device is worn. In yet other embodiments, the light-blocking element 108 extends from the surface on which the light source(s) 114 and the light detector(s) 112 are disposed to an optically-opaque portion of the material 108 (e.g., silicone gel) disposed between the prisms and the skin of the ear canal when the PPG device 100 is worn.

In some cases, the width of the light-blocking element 108 (e.g., measured in a circumferential direction of the ear canal) is equal to (or substantially equal to) the distance between the light source(s) 114 and the light detector(s) 112. In other cases, the width of the light-blocking element 108 is smaller than the distance between the light source(s) 114 and the light detector(s) 112.

Separation Distance Optimization

As opposed to the example embodiments shown, if the light source(s) 114 and the light detector(s) 112 were facing in directly opposite directions (e.g., emitter facing left, and photodiode facing right in FIG. 1), almost no light emitted by the light source(s) 114 would return back to the light detector(s) 112. Similarly, it may be said that if the emitter field management element (e.g., prism) were to cause the light emitted from the light source(s) 114 to travel in a direction opposite to the light detector(s) 112 (e.g., towards the left in FIG. 1), almost no light emitted by the light source(s) 114 may return back to the light detector(s) 112. On the other hand, if the light source(s) 114 and the light detector(s) 112 were facing the same direction (e.g., both facing down), or facing into each other (e.g., with the angle between the direction in which the light is emitted and received being less than 90 degrees), the light emitted by the light source(s) 114 would experience a minimal amount of modulation due to the short distance between the light source(s) 114 and the light detector(s) 112 under the skin of the ear canal. Thus, in some embodiments described herein, the angle between the directions in which the light is emitted and is received may be large enough to cause the light to travel a threshold distance underneath the skin of the ear canal but small enough to cause a threshold amount (e.g., percentage or portion) of the light emitted by the light source(s) 114 is returned to the light detector(s) 112. Similarly, if the emitter field management element were to cause the light emitted from the light source(s) 114 to travel directly into the inner wall of the ear canal (e.g., towards the bottom in FIG. 1) or travel towards the light detector(s) 112 (e.g., towards the right in FIG. 1), the light emitted by the light source(s) 114 may experience a minimal amount of modulation due to the relatively short distance between the light source(s) 114 and the light detector(s) 112 under the skin of the ear canal. Thus, in some embodiments described herein, the characteristics of the emitter light field management element and/or the detector light field management element are designed such that the refraction through the elements (e.g., lenses thereof) causes the light to travel at least a threshold distance underneath the skin of the ear canal, but at the same time causing at least a threshold amount (e.g., percentage or portion) of the light emitted by the light source(s) 114 to be returned to the light detector(s) 112.

PPG Sensor Placement within Ear Canal

Figure 2:
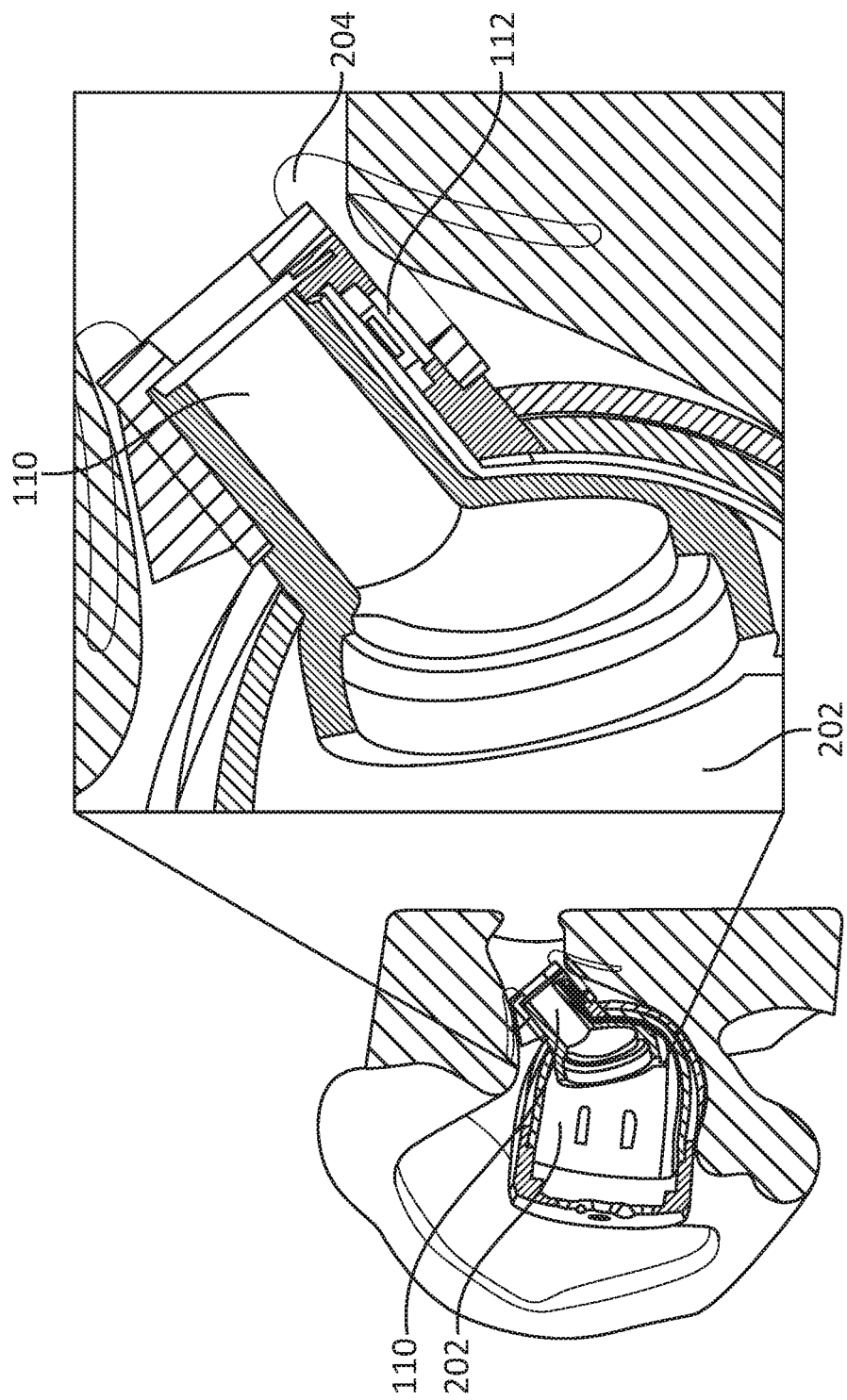
FIG. 2 illustrates another cross-sectional view of an example in-ear heart rate monitoring device in accordance with aspects of this disclosure.

FIG. 2 shows another cross-sectional view of the PPG device 100 of FIG. 1 according to some embodiments. As illustrated in FIG. 2, the PPG sensor disposed within the audio port 110 portion of the PPG device or on the outer surface 202 of the audio port 110 is positioned against the skin (inner wall) of the ear canal when the PPG device is worn by the user. The placement of the PPG sensor against the skin may be facilitated using the silicone gels (e.g., outer tip 204), or flexible covering comprising other material, shown in FIG. 2, which may be designed to fit snugly inside the ear canal. The flexible covering (e.g., outer tip 204) may comprise silicone gel, or other flexible material having desirable plasticity to provide comfort and allow for conformability for fitting snugly within a human ear. The flexible covering (e.g., outer tip 204) may at least partially cover the audio port 110 as shown in FIG. 2, and may be replaceable and/or available in various sizes, colors, etc. At least some portions of the flexible covering (e.g., outer tip 204) of the audio port 110 may be transparent, and the flexible covering (e.g., outer tip 204) may secure the PPG device at least partially inside the ear canal, such that the light sources(s) and the light detector(s) 112 (or the surface on which the light source(s) and the light detector(s) are both disposed) are facing the inner wall of the ear canal.

As shown in FIG. 2, the audio port 110 may generally point into the ear canal. The audio port 110 may provide sound based on audio data received from another device such as a smartphone or an MP3 player. The PPG sensor may be placed at a specific location within the audio port 110, such that when the PPG device (e.g., earbud, headphone, etc.) is properly worn by the user (e.g., with the tip of the audio port 110 pointing directly into the ear canal and the flexible covering (e.g., outer tip 204) snugly fitted inside the ear canal), the emitter light field management element (e.g., prism) causes the light emitted by the light source(s) to go through the skin (e.g., inner wall) of the ear canal and the detector light field management element (e.g., prism) is positioned such that the light reflected through the skin (e.g., inner wall) of the ear canal is refracted by the detector light field management element towards the light detector(s) 112.

Flexible Audio Port Covering and PPG Sensor

Figure 3B:
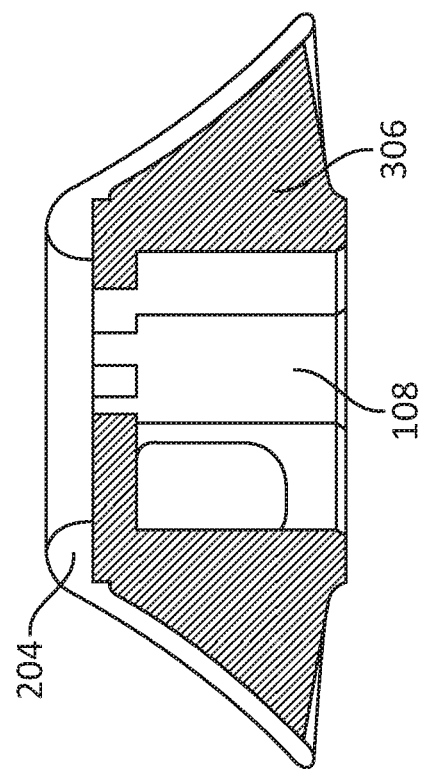
FIGS. 3A and 3B illustrate an optically opaque silicone layer and an optically transparent silicone layer of an example in-ear heart rate monitoring device in accordance with aspects of this disclosure.
Figure 3A:
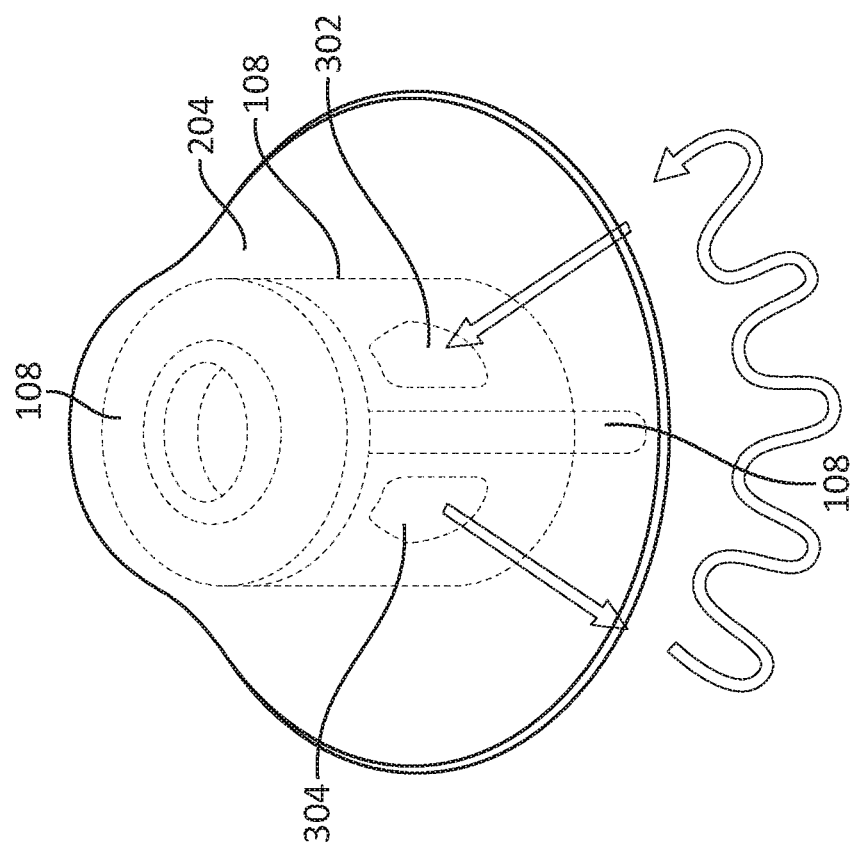

FIGS. 3A and 3B illustrate perspective and cross-sectional views of flexible audio port coverings (e.g., outer tip 204 and light-blocking element 108) according to one or more embodiments of the present disclosure. In certain embodiments, the flexible coverings may comprise replaceable gel forms (e.g., one or more layers of silicone gel) that are configured to cover the outside of the audio port including the PPG sensor. In some embodiments, these flexible coverings are identical or similar in shape and function to replaceable earbud tips used to cover certain earbud speakers. Alternatively, in some other embodiments, the PPG sensor may be associated with the flexible covering (instead of on or within the audio port), and/or the flexible covering may be integrated into the PPG device. In some embodiments, one or more portions of the flexible covering (e.g., outer tip 204 and light-blocking element 108) are configured to be removable from the audio port or another portion of the PPG device. In some embodiments, one or more portions of the flexible covering (e.g., outer tip 204 and light-blocking element 108) are configured to be affixed to the audio port or another portion of the PPG device.

FIGS. 3A and 3B show two types of flexible covering portions (e.g., silicone gel forms) that may be shaped and/or configured to cover the audio port that includes the PPG sensor. The first type (e.g., outer tip 204) may comprise an optically-transparent silicone gel, or other material, that lets light emitted by the light source(s) and the light reflected towards the light detector(s) through the optically transparent covering material. The second type (e.g., light-blocking element 108) illustrated may comprise an optically-opaque silicone gel, or other material, that is configured to at least partially block the light emitted by the light sources(s) and the light reflected towards the light detector(s). The optically-opaque covering material (e.g., material of outer tip 204) may comprise a light emitter window 304 and a light detector window 302, such that at least part of the light emitted by the light source(s) goes through the emitter window 304 and at least part of the light reflected towards the light detector(s) goes through the light detector window 302. In some embodiments, the PPG device includes the optically-transparent covering material (e.g., material of outer tip 204) that covers the audio port but does not include the optically-opaque covering material (e.g., material of light-blocking element 108). In some other embodiments, the PPG device includes both the optically-transparent material (e.g., material of outer tip 204) and the optically-opaque material (e.g., material of light-blocking element 108) covering the audio port. In yet other embodiments, the PPG device includes a flexible covering (e.g., silicone gel) having some portions that are optically-transparent and other portions that are optically-opaque.

Light-Blocking Structures

FIG. 3A shows a light-blocking rib, which may comprise a light-blocking wall (e.g., at least a portion of light-blocking element 108) that is disposed between the light emitter(s) and the light detector(s) (e.g., photodiode) to at least partially prevent the light emitted by the light emitter(s) from travelling straight into the light detector(s). In some embodiments, the light-blocking rib extends (e.g., in a radial direction away from the axis of the audio port) all the way to the skin (e.g., inner wall) of the ear canal. Alternatively, one or more layers of optically-transparent material (e.g., silicone gel) may be placed between the skin of the ear canal and the light-blocking rib. In some cases, the light-blocking rib is provided in addition to the light blocking element shown in FIG. 1. In other cases, the light-blocking rib is omitted from the audio port covering. In yet other cases, the light-blocking rib extends from the end of the light blocking element of FIG. 1 that is farthest away from the axis of the audio port to the skin (e.g., inner wall) of the ear canal.

In some cases, the width of the light-blocking rib (e.g., measured in a circumferential direction of the ear canal) is equal to (or substantially equal to) the distance between the light emitter(s) and the light detector(s). In other cases, the width of the light-blocking rib is smaller than the distance between the light emitter(s) and the light detector(s).

The PPG device may include multiple light-blocking ribs to better prevent light from going from the light emitter(s) to the light detector(s) without going through the skin of the user. For example, FIG. 3B illustrates an example in which two light-blocking ribs are provided, one between the emitter/detector windows, and the other on the opposite side of the audio port.

Light Emitter/Detector Windows

As shown in FIG. 3A, the optically-opaque covering material 108 (e.g., silicone gel) may comprise one or more windows (e.g., windows 302 and 304) for controlling the light travel in and/or out of the PPG sensor. In some embodiments, the emitter window 304 is parallel (or substantially parallel) to the surface of the emitter light field management element (e.g., prism) that is closest to the emitter window, and the light detector window 302 is parallel (or substantially parallel) to the surface of the detector light field management element (e.g., prism) that is closest to the detector window 302. The light-blocking rib may bisect (or substantially bisect) the angle between the emitter direction perpendicular to the surface of the emitter light field management element closest to the emitter window 304 (or to an inner wall of the ear canal) and the light detector direction perpendicular to the surface of the detector light field management element closest to the light detector window 302 (or to an inner wall of the ear canal). In some embodiments, the optically-opaque covering of inner tip 108 may only include the light-blocking rib(s) such that the emitter/detector windows 304 and 302 at least partially encompass any portion of the covering that does not include the light-blocking rib(s).

Depending on the width of the user's ear canal, the light-blocking rib and/or the emitter/detector windows 304 and 302 may be adjusted. In some embodiments, the light-blocking rib and/or the emitter/detector windows 304 and 302 are adjusted by replacing the flexible covering of outer tip 204 with another that has a different size or shape. In some cases, the flexible covering 204 may be optimized for specific skin tones such that a covering designed for one skin tone has larger windows and/or smaller light-blocking rib(s), whereas a covering designed for another different skin tone has smaller windows and/or larger light-blocking rib(s). By using the light-blocking rib(s) and the emitter/detector windows, the light emitter/detector separation distance can be adjusted possibly without having to move any electronic components.

Location of PPG Sensor

In some embodiments, the PPG device may be designed such that when the light emitter(s) emit light (e.g., from one or more LEDs), the amount of light going through the user's skin inside the ear canal is maximized (or above a threshold level). However, doing so by placing the PPG sensor directly against the skin may cause discomfort and/or cause the PPG device to move around inside the user's ear. Thus, the PPG device may include one or more layers of transparent covering material (e.g., silicone gel) covering the PPG sensor and/or the rigid audio port, thereby advantageously providing user comfort, improved fitting, and/or maximum (or improved) light transmission through the skin inside the ear canal.

Due to the variability of ear sizes and ear canal sizes, it may be difficult to design the PPG device such that the PPG sensor is positioned directly against the skin when the PPG device is worn. By placing the PPG sensor on or inside the rigid audio port and not on the flexible covering (e.g., gel form) itself (thereby decoupling the PPG sensor and the flexible covering), the user may simply choose a replaceable covering tip that fits his or her ear canal, and therefore the same PPG device can be used to accommodate a wider range of users.

Further, by decoupling the PPG sensor and the flexible covering, if the covering is damaged, only the covering may need to be replaced (not the entire PPG device). Additionally, the covering may protect the electronics in the PPG device and/or serve as a controllable barrier that can be customized without having to modify the rest of the PPG device.

Angle Between Light Emitter(s) and Light Detector(s)

Using light field management elements (e.g., prisms) in accordance with the present disclosure to angle the light emitted from the light emitter(s) away from the light detector(s) (e.g., photodiode(s)) and to angle the light reflected through the skin towards the light detector(s) may cause the light emitted by the light emitter(s) to travel a greater distance underneath the skin inside the ear canal before being reflected back to the light detector(s). By doing so, PPG devices in accordance with the present disclosure may allow for the sensor data generated by the light detector(s) to include a greater amount of (or better quality) pulse/cardiac component, thereby improving the accuracy of heart rate (HR) measurements performed by the PPG device. In some embodiments, the angle between the emitter angle at which the light emitter(s) emit light and the directed emitter angle at which the emitted light exits the prism, or other light field management element(s), is greater than 0 degrees and less than 90 degrees. For example, the angle may be between 30 degrees and 60 degrees. Similarly, the angle between the reflection angle at which the reflected light enters the prism, or other light field management element(s), and the directed reflection angle at which the directed reflected light is received at the light detector(s) is greater than 0 degrees and less than 90 degrees. For example, the angle may be between 30 degrees and 60 degrees.

In some embodiments, the distance between the light emitter(s) and the light detector(s) is less than a predetermined threshold. The predetermined threshold may be the width of the ear canal. Alternatively, the predetermined threshold may be a fraction of the width of the ear canal. In some cases, the predetermined threshold may be the width of the audio port. Alternatively, the predetermined threshold may be a fraction of the width of the audio port.

Adjusting the PPG Sensor Placement Using Audio

The accuracy of heart rate (HR) measurements can be relatively sensitive to whether or not the PPG sensor(s) are positioned properly against the skin. In some embodiments, the PPG sensor placement inside the ear canal may be adjusted (or improved) using the audio played by the earbud. For example, the PPG device may be designed such that the optimal PPG sensor placement against the skin inside the ear canal (e.g., to result in optimal light field management) coincides with the optimal earbud placement inside the ear for achieving the highest sound quality. If the user of the PPG device (e.g., earbud that also monitors heart rate) determines that the quality of the sound played by the earbud is low (e.g., music volume is low), the user may reposition the PPG device inside the user's ear until the sound quality expected by the user is achieved. By repositioning the PPG device to improve the sound quality (e.g., so that the sound played by the earbud is more clearly heard), the signal quality of the PPG sensor is also improved (e.g., reduced amount of ambient light detected by the light detector(s) (e.g., photodiode(s)), improved positioning of the sensors against the skin, etc.).

Structural Relationship Between Audio Port and PPG Sensor

The surface of the PPG sensor package on which the light emitter(s) and the light detector(s) (e.g., photodiode(s)) are disposed may be substantially parallel to the axis of the portion of the audio port that partially goes into the ear canal when the PPG device is worn (e.g., the portion of the purple component in FIG. 2 that is inserted into the ear canal).

The width of the audio port of the PPG device (e.g., in a cross-section perpendicular to the axis of the audio port) may be sized such that if the light emitter(s) and the light detector(s) were spaced apart from each other by the width of the audio port and facing the same direction (e.g., towards the bottom in FIG. 1), the resulting HR measurement may not be sufficiently accurate (e.g., accuracy above a threshold). The width of the audio port may be smaller than an emitter/detector separation that would result in HR measurement exceeding a quality or accuracy threshold if the light emitter(s) and the light detector(s) were facing the same direction.

In some embodiments, the direction in which the sound provided by the earbud speaker through the audio port travels is perpendicular (or substantially perpendicular) to the surface on which the light emitter(s) and the light detector(s) are disposed. In some embodiments, the light emitter(s) and the light detector(s) may be aligned along an axial direction of the audio port (or the direction in which the sound provided by the earbud speaker through the audio port travels).

Alternative Embodiments

In other embodiments, in-ear heart rate monitors may read from two alternate locations in the ear, either the auditory meatus (the flattish area of the concha near the canal) or the bottom of the concha behind the antitragus. Another way of performing HR measurement from inside the ear canal might be to position the PPG sensor in the audio port so that the LED shines directly down the ear canal. Yet another embodiment might be to place the PPG sensors in the earphone tip itself, so that the sensor is in direct contact with the skin. Since the ear tips are interchangeable for different sizes, this may mean that a PPG sensor would need to be provided with each set of ear tips.

Light field management elements in accordance with the present disclosure may take any desirable or suitable type or form. For example, light field management elements in accordance with the present disclosure may comprise one or more prisms. Alternatively, Fresnel lenses may be utilized instead of simple prisms, which may advantageously allow the size of the package to be reduced and facilitate shaping of the light. In some cases, the PPG sensor manufacturer may mold the light field management elements (e.g., prisms) as part of a manufacturing process. Alternatively, the light field management elements (e.g., prisms) may be bonded to the PPG sensor after the PPG sensor has been manufactured. Although prisms are used in some embodiments of the present disclosure, the techniques described herein may be extended to other light field management elements, such as light pipes, total internal reflection mirrors, metallized mirrors, diffractive optical elements, back reflectors, to name a few examples.

Light Source

Although light sources for use in PPG sensor devices are described herein primarily in a generic sense, in various embodiments, the light source(s) of a PPG sensor may comprise one or more electronic semiconductor light sources, such as LEDs, or produce light using any of filaments, phosphors, or laser, or other type of light source. In some implementations, the center wavelengths of the light emitted by the light source(s) described herein may be in the range of 495 nm to 570 nm. For example, a particular green light source may emit light with a center wavelength of 528 nm. In other embodiments, the light source may emit red light (e.g., 660 nm center wavelength) or IR light (e.g., 940 nm center wavelength). In some embodiments, the light source emits light having a narrow range angle (e.g., narrow range angle laser).

The spacing between the light source and the light detector may be measured from the side of the light source/detector or the center of the light source/detector. For example, the source and detector may be positioned in the PPG device such that the center of the light source is less than a particular distance from the edge of the light detector. In some embodiments, the particular distance may be one of 1 mm, 2 mm, and 3 mm. In some embodiments, the particular distance may be the width of the audio port of the PPG device (or a fraction of the width of the audio port). The particular magnitude of the spacing may depend on a number of factors and this disclosure does not limit the embodiments to any particular spacing.

Light Detector

Although primarily described herein with reference to photodiode light detectors, in various embodiments, the light detector of a PPG sensor may comprise one or more sensors that is/are adapted to detect wavelengths of light emitted from the light source. A particular light source combined with a particular detector may comprise a sensor such as a PPG sensor. A light detector, in an embodiment, may comprise one or more detectors for detecting each different wavelength of light that is used by the light sources. For example, a first detector may be configured to detect light with a wavelength of 560 nm, a second detector may be configured to detect light with a wavelength of 940 nm, and a third detector may be configured to detect light with a wavelength of 528 nm. Examples include photodiodes fabricated from semiconductor materials and having optical filters that admit only light of a particular wavelength or range of wavelengths. The light detector may comprise any of a photodiode, phototransistor, charge-coupled device (CCD), thermopile detector, or complementary metal-oxide-semiconductor (CMOS) sensor. The light detector may comprise multiple detector elements. One or more of the detectors may comprise a bandpass filter circuit.

In other embodiments, the light detector comprises one or more detectors configured to detect multiple wavelengths of light. For example, a single detector may be configured to tune to different frequencies based on data received from an electrical digital microprocessor coupled to light detectors. In another way, the single detector may include multiple active areas where each active area is sensitive to a given range of wavelengths. In an embodiment, a single detector is configured to detect light with wavelengths in the red and IR frequencies and a second detector is configured to detect light with wavelengths in the green frequencies. Further, each light source may use any of one or more different wavelengths of light as previously described.

In an embodiment, the light detector is mounted on the audio port of the PPG device with one or more filters that are configured to filter out wavelengths of light other than wavelengths emitted by the light source of the PPG device. For example, a portion of the audio port or the silicone gel of the PPG device may be covered with a filter which removes ambient light other than light in wavelengths emitted by the light source. For example, signals from the light source may be received at the light detector through an ambient light filter that filters out an ambient light source that generates an ambient light with a wavelength that is different from the wavelength that is detected by the light detector. Although an LED and a photodiode are used as examples of the light source and the light detector, respectively, the techniques described herein may be extended to other types of light sources and detectors. For example, the PPG device may include (i) single or multiple LEDs and a multi-element photodetector (e.g., a camera sensor), (ii) an LED array and single or multiple photodiodes, (iii) spatial light modulator (SLM) (e.g., a digital micromirror device

[DMD] or a liquid crystal on silicon [LCoS] device) and single or multiple LEDs, other combinations thereof, or other configurations of light sources and detectors.

Detection of In-Canal Status of PPG Device

The various embodiments of PPG devices described herein may be designed to detect whether or not the PPG device is worn by the user. For example, the processor of the PPG device may monitor an output signal of the PPG sensor and determine, based on the output signal, whether or not the PPG device is worn by the user.

For example, the processor of the PPG device may monitor, based on output of the PPG sensor, at least one characteristic of a heartbeat waveform of the user of the PPG device. In particular, by analyzing output from the PPG sensor, the processor may be able to verify whether the output from the PPG sensor is consistent with the PPG device being worn. For example, the processor may determine whether the output signal of the PPG sensor is representative of a cardiac signal. When the output signal of the PPG sensor is not representative of a cardiac signal, the processor may determine that the PPG device is not worn (or not properly worn). In response to such a determination, the PPG device may deactivate one or more components of the PPG device (e.g., wireless communication or Bluetooth module, PPG sensor, audio module, and/or any other component of the PPG device) to conserve power.

In some embodiments, the PPG device may determine, based on the output signal of the PPG sensor, whether or not the PPG device is properly worn (e.g., in a manner that would yield HR measurement above a threshold accuracy level) by the user. Based on a determination that the PPG device is worn but not properly worn by the user, the PPG device may provide an alert (e.g., auditory or haptic) to the user to signal to the user that the PPG device is not properly worn by the user.

In some cases, IR light may be used to detect an in-canal status of the PPG device. In such cases, the PPG device may monitor the total amount of reflected IR light received by the light detector(s). Based on the total amount exceeding a threshold, the PPG device may determine that the PPG device is worn by the user. In other cases, green light may be used to detect an in-canal status of the PPG device. In such cases, the PPG device may monitor the strength of the cardiac component in the output signal, and based on the strength of the cardiac component exceeding a threshold, the PPG device may determine that the PPG device is worn by the user.

Example Wearable Device Architecture

Figure 4:
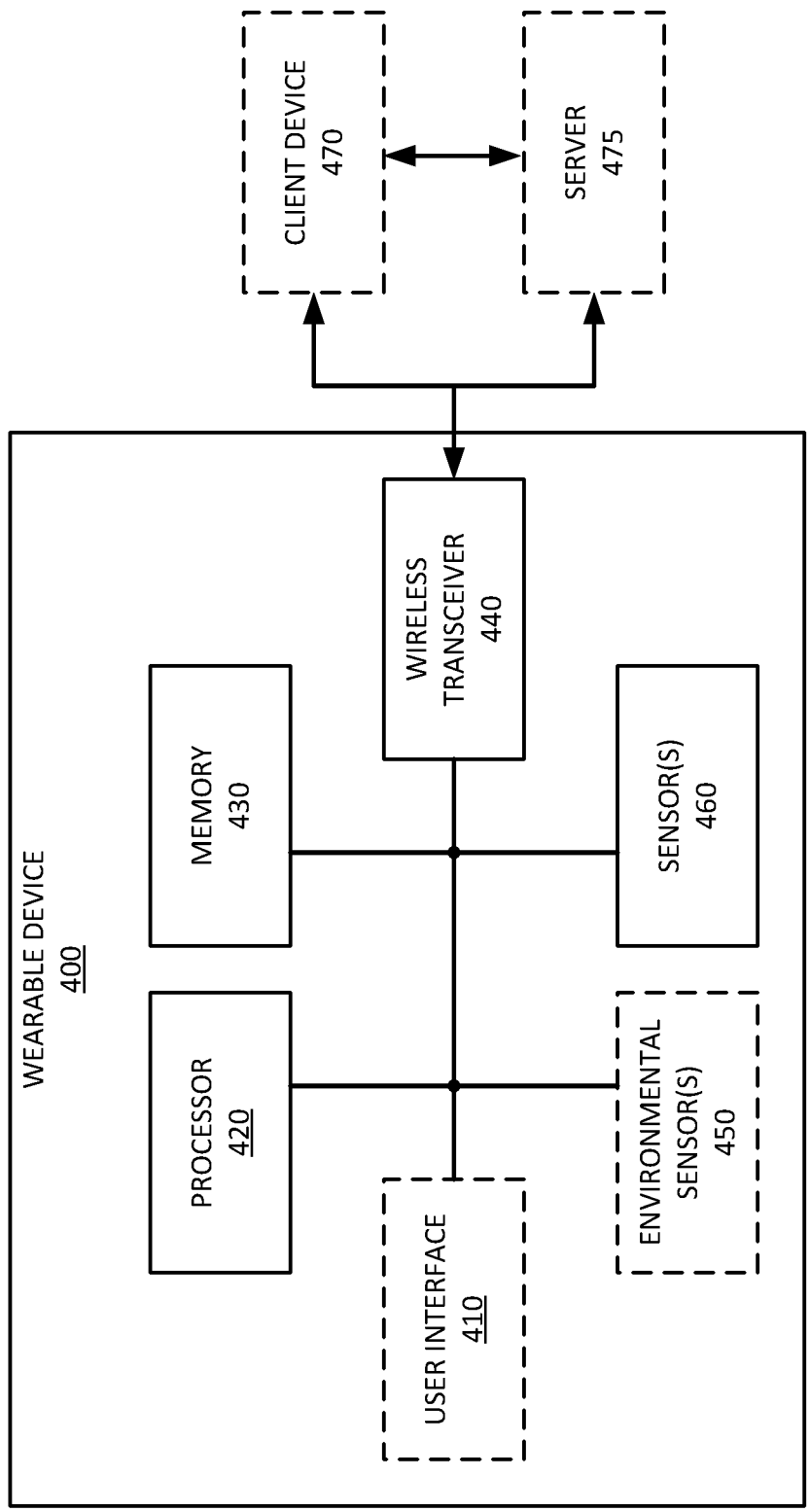
FIG. 4 is a block diagram illustrating certain components of an example wearable device in accordance with aspects of this disclosure.

FIG. 4 is a block diagram illustrating an example wearable device (e.g., the PPG device 100 described herein) in accordance with aspects of this disclosure. The wearable device 400 may include a processor 420, a memory 430, a wireless transceiver 440, and one or more sensor(s) 460. The wearable device 400 may also optionally include a user interface 410 and one or more environmental sensor(s) 450. The wireless transceiver 440 may be configured to wirelessly communicate with a client device 470 and/or server 475, for example, either directly or when in range of a wireless access point (not illustrated) (e.g., via a personal area network (PAN) such as Bluetooth pairing, via a wireless local area network (WLAN), etc.). Each of the memory 430, the wireless transceiver 440, the one or more sensor(s) 460, the user interface 410, and/or the one or more environmental sensor(s) 450 may be in electrical communication with the processor 420.

The memory 430 may store instructions for causing the processor 420 to perform certain actions. The memory 430 may include modules for performing one or more elements of the methods/processes described in the present disclosure. Memory 430 may include a non-transitory computer-readable storage medium. In some embodiments, the sensors 460 may include one or more of biometric sensors, optical sensors (e.g., a photoplethysmographic (PPG) sensor), inertial sensors (e.g., accelerometer, gyroscope, etc.), barometric sensors (e.g., altimeter, etc.), geolocation sensors (e.g., GPS receiver), and/or other sensor(s). Further information regarding such sensors is described in more detail below (e.g., in connection with FIG. 4).

The wearable device 400 may collect one or more types of physiological and/or environmental data from the one or more sensor(s) 460, the one or more environmental sensor(s) 450, and/or external devices and communicate or relay such information to other devices (e.g., the client device 470 and/or the server 475), thus permitting the collected data to be viewed, for example, using a web browser or network-based application. For example, while being worn by the user, the wearable device 400 may perform biometric monitoring via calculating and storing the user's step count using the one or more sensor(s) 460. The wearable device 400 may transmit data representative of the user's step count to an account on a web service (e.g., www.fitbit.com), computer, mobile phone, and/or health station where the data may be stored, processed, and/or visualized by the user. The wearable device 400 may measure or calculate other physiological metric(s) in addition to, or in place of, the user's step count. Such physiological metric(s) may include, but are not limited to: energy expenditure, e.g., calorie burn; floors climbed and/or descended; heart rate; heartbeat waveform; heart rate variability; heart rate recovery; respiration, oxygen saturation (SpO2), blood volume, blood glucose, skin moisture and skin pigmentation level, location and/or heading (e.g., via a GPS, global navigation satellite system (GLONASS), or a similar system); elevation; ambulatory speed and/or distance traveled; swimming lap count; swimming stroke type and count detected; bicycle distance and/or speed; blood pressure; blood glucose; skin conduction; skin and/or body temperature; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 400 may also measure or calculate metrics related to the environment around the user (e.g., with the one or more environmental sensor(s) 450), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 400 (and/or the client device 470 and/or the server 475) may collect data from the sensor(s) 460 and/or the environmental sensor(s) 450, and may calculate metrics derived from such data. For example, the wearable device 400 (and/or the client device 470 and/or the server 475) may calculate the user's stress or relaxation levels based on a combination of heart rate variability, skin conduction, noise pollution, and/or sleep quality. In another example, the wearable device 400 (and/or the client device 470 and/or the server 475) may determine the efficacy of a medical intervention, for example, medication, based on a combination of data relating to medication intake, sleep, and/or activity. In yet another example, the wearable device 400 (and/or the client device 470 and/or the server 475) may determine the efficacy of an allergy medication based on a combination of data relating to pollen levels, medication intake, sleep and/or activity. These examples are provided for illustration only and are not intended to be limiting or exhaustive.

Physiological Sensor Reading Assessment Server

A PPG reading assessment system may implement a server system 475 to collect detected physiological sensor readings from one or more wearable computing devices such as wearable device 400 and/or client device 470 as shown. In some implementations, server system 475 may also collect detected physiological sensor readings and/or calculated metric values directly from one or more wearable computing devices 400 and/or indirectly from one or more client devices 470 as shown. For example, wearable computing device 400 may not be associated with an external computing device, therefore it may transmit collected physiological data (e.g., PPG readings) while user is wearing device 400 to server system 475, which analyzes the received data to determine values of one or more physiological metrics (e.g., a heart rate), to transmit back to wearable computing device 400. In another example, wearable computing device 400 transmits collected physiological data of a user to both server system 475 and client device 470. In this example, client device 470 may determine values for one or more physiological metrics (e.g., heart rate), while server system 475 uses the received physiological data to update a user profile for the user, stored (e.g., in a profiles database).

In some implementations, server system 475 is implemented on one or more standalone data processing apparatuses or a distributed network of computers. In some embodiments, server system 475 also employs various virtual devices and/or services of third party service providers (e.g., third-party cloud service providers) to provide the underlying computing resources and/or infrastructure resources of server system 475. In some embodiments, server system 475 includes, but is not limited to, a handheld computer, a tablet computer, a laptop computer, a desktop computer, or a combination of any two or more of these data processing devices or other data processing devices.

Server system 475 may include one or more processors or processing units (e.g., CPUs) and one or more network interfaces including an I/O interface to client computing devices and wearable computing devices. In some implementations, server system 475 includes memory, and one or more communication buses for interconnecting these components. Memory of server 475 may include high-speed random access memory, such as DRAM, SRAM, DDR RAM, or other random access solid state memory devices; and, optionally, may include non-volatile memory, such as one or more magnetic disk storage devices, one or more optical disk storage devices, one or more flash memory devices, or one or more other non-volatile solid state storage devices. Memory of server 475, optionally, includes one or more storage devices remotely located from one or more of the processing units of server 475. Memory of server 475, or alternatively the non-volatile memory within the memory of server 475, includes a non-transitory computer readable storage medium. In some implementations, the memory of server 475, or the non-transitory computer readable storage medium of the memory of server 475, stores one or more programs, modules, and data structures. These programs, modules and data structures may include, but not be limited to one or more of an operating system including procedures for handling various basic system services and for performing hardware dependent tasks, a network communication module for connecting server system 475 to other computing devices (e.g., wearable computing devices 400 and/or client computing devices 470) connected to one or more networks via one or more network interfaces (wired or wireless).

Measuring Heart Rate and/or Heart Rate Variability

Figure 5:
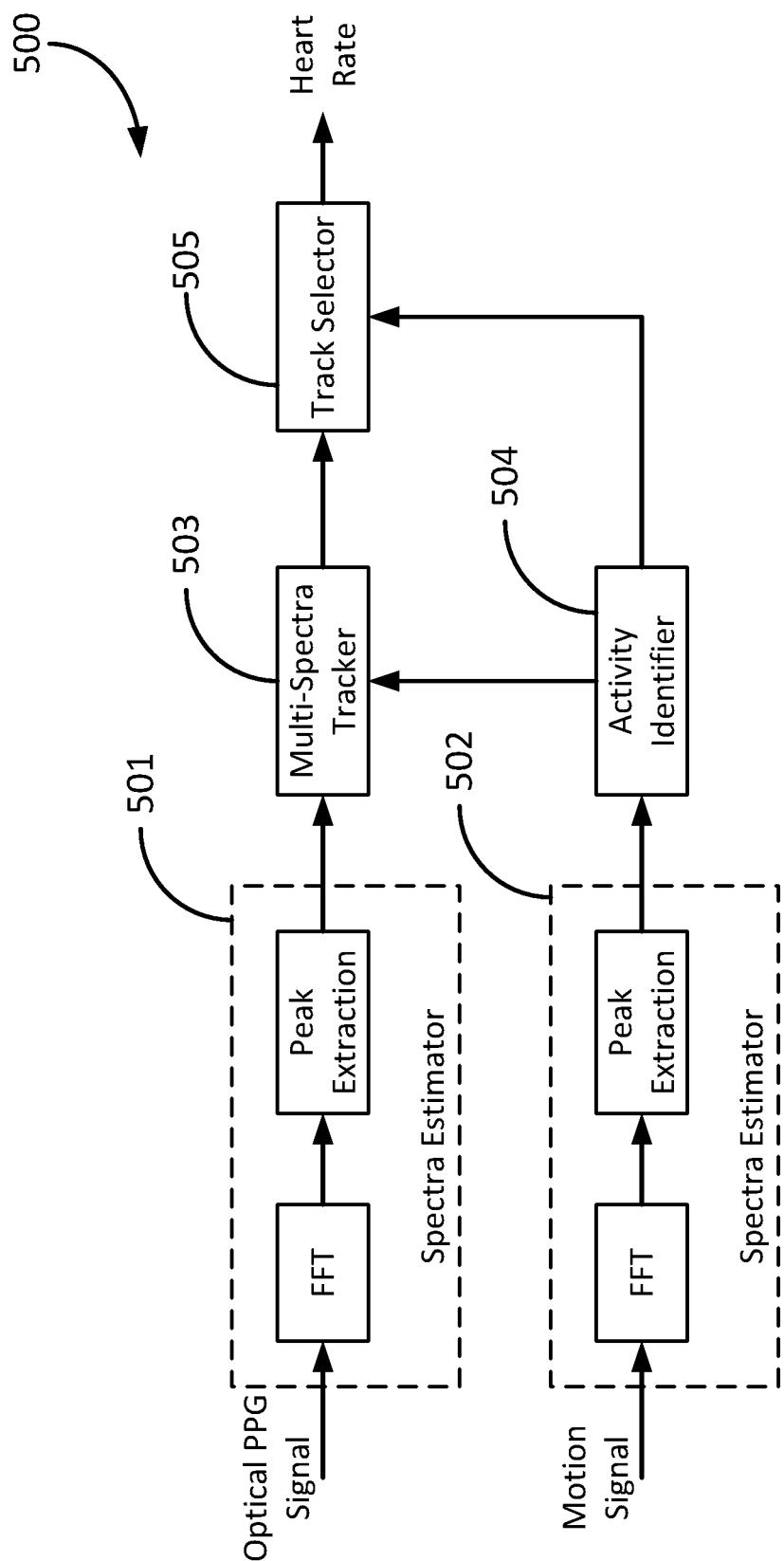
FIG. 5 is an example block diagram of a system used for determining HR estimate in accordance with aspects of this disclosure.

FIG. 5 is an example block diagram of a system used for determining HR in accordance with aspects of this disclosure. As shown in FIG. 5, the PPG device may include a system 500 of circuit components for determining the HR of the user based on an optical PPG signal (e.g., received by one or more light detectors of the PPG device) and a motion signature (e.g., received from an accelerometer in the PPG device). As used herein, a motion signature may refer to any biometric signature or signal that may be received from and/or based on output data from one or more of sensors, such as, for example, inertial sensor(s) (e.g., accelerometer(s) and gyroscope(s)), barometric sensors(s) (e.g., altimeter(s)), which may be indicative of the activity and/or physiological state of a user of the PPG device. The system 500 may be implemented by hardware components and/or in software executed by the processor. The system 500 may include first and second spectra estimators 501 and 502, a multi-spectra tracker 503, an activity identifier or discriminator 504, and a track selector 505. Each of the first and second spectra estimators 501 and 502 may include a Fast Fourier Transform (FFT) block and a peak extraction block. In the example of FIG. 5, the activity identifier 504 may use the peaks extracted from the motion signature to determine the activity that the user is performing (e.g., sedentary, walking, running, sleeping, lying down, sitting, biking, typing, elliptical, weight training, swimming, etc.). This determination of the current activity of the user may be used by the multi-spectra tracker 503 and the track selector 505 in extracting the HR from the optical PPG signal. Thus, the motion signature in FIG. 5 may be used by the system 500 to determine the current activity of the user. In other embodiments, the processor may use a technique similar to that of the activity identifier 504 in determining the type of an exercise, as discussed in greater detail below.

The blocks illustrated in FIG. 5 are merely examples of components and/or processing modules that may be performed to supplement a PPG signal with a motion signature to determine HR. However, in other implementations, the system 500 may include other blocks or may include input from other biometric sensors of the PPG device.

Under certain operating conditions, the HR of the user may be measured by counting the number of signal peaks within a time window or by utilizing the fundamental frequency or harmonic frequency components of the signal (e.g., via an FFT). In other cases, such as HR data acquired while the user is in motion, FFTs may be performed on the signal and spectral peaks extracted, which may then be subsequently processed by a multiple-target tracker which starts, continues, merges, and/or deletes tracks of the spectra.

In some embodiments, a similar set of operations may be performed on the motion signature and the output may be used to perform activity discrimination which may be used to assist the multi-spectra tracker 503. For instance, it may be determined that the user was stationary and has begun to move. This information may be used to by the multi-spectra tracker 503 to bias the track continuation toward increasing frequencies. Similarly, the activity identifier 504 may determine that the user has stopped running or is running slower and this information may be used to preferentially bias the track continuation toward decreasing frequencies.

Tracking may be performed by the multi-spectra tracker 503 with single-scan or multi-scan, multiple-target tracker topologies such as joint probabilistic data association trackers, multiple-hypothesis tracking, nearest neighbor, etc. Estimation and prediction in the tracker may be done through Kalman filters, spline regression, particle filters, interacting multiple model filters, etc.

The track selector 505 may use the output tracks from the multiple-spectra tracker 503 and estimate the user's heart rate based on the output tracks. The track selector 505 may estimate a probability for each of the tracks that the corresponding track is representative of the user's heart rate. The estimate may be taken as the track having the maximum probability of being representative of the user's heart rate, a sum of the tracks respectively weighted by their probabilities of being representative of the user's the heart rate, etc. The activity identifier 504 may determine a current activity being performed by the user which may be used by the track selector 505 in estimating the user's heart rate. For instance, when the user is sleeping, sitting, lying down, or sedentary, the user's estimated heart rate may be skewed toward heart rates in the 40-80 bpm range. When the user is running, jogging, or doing other vigorous exercise, the user's estimated heart rate may be skewed toward elevated heart rates in the 90-180 bpm range. The activity identifier 504 may determine the user's current activity (e.g., a current exercise) based at least in part on the speed of the user. The user's estimated heart rate may be shifted toward (or wholly obtained by) the fundamental frequency of the selected output track when the user is not moving. The output track that corresponds to the user's heart rate may be selected by the track selector 505 based on criteria that are indicative of changes in activity. For instance, when the user begins to walk from being stationary, the track selector 505 may select the output track that illustrates a shift toward higher frequency based on output received from the activity discriminator 504.

Although some embodiments of the present disclosure are described with respect to HR, the techniques described herein may be extended to other metrics. For example, sensor data generated by the one or more sensors described herein may be used to determine respiration, SpO2, blood volume, blood glucose, skin moisture, and skin pigmentation level and, for example, utilize such metrics for activity detection/identification.

Methods for Providing a Wearable Device

Figure 6:
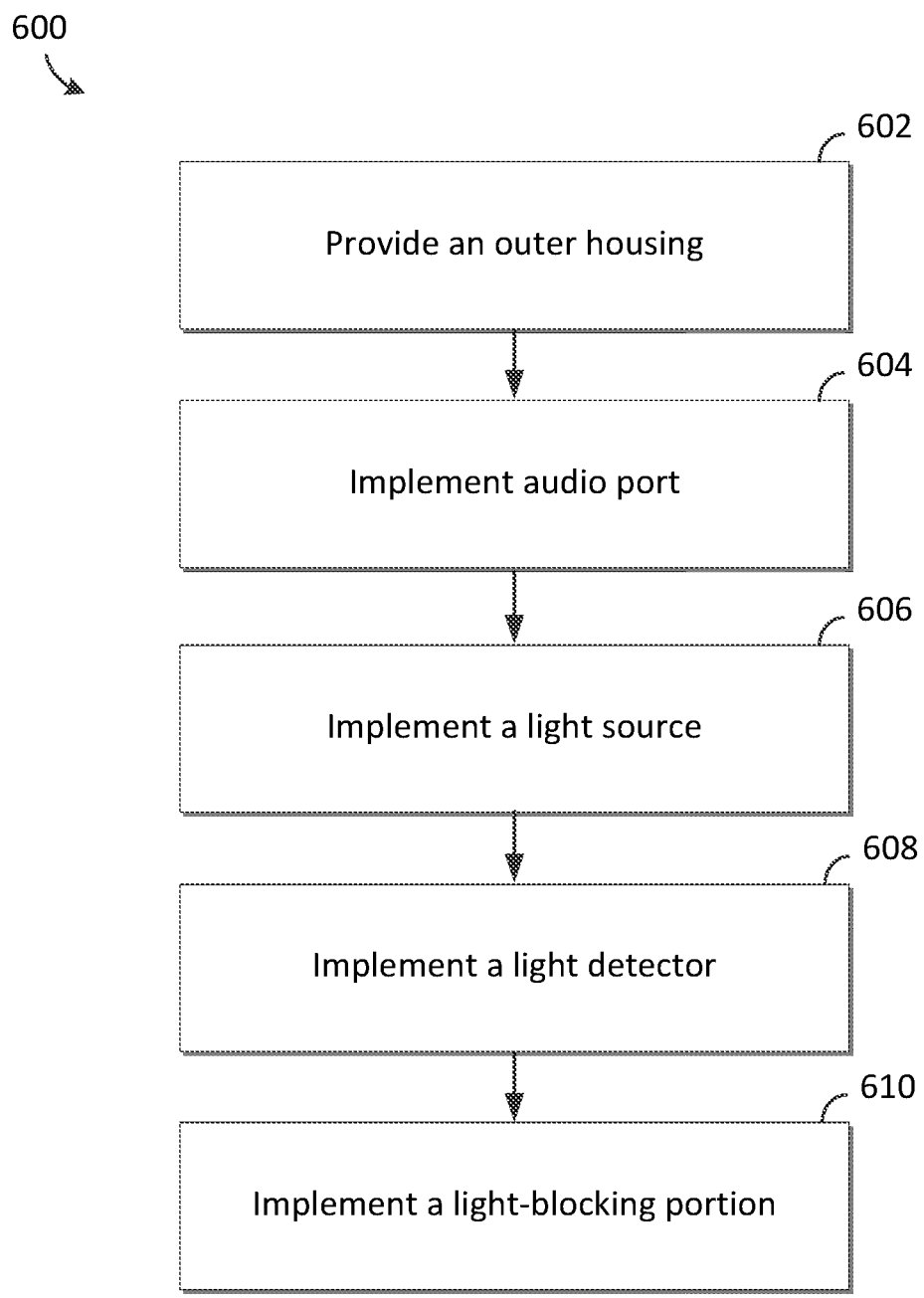
FIG. 6 is an example flow diagram of a process for providing a wearable computing device in accordance with aspects of this disclosure.

FIG. 6 illustrates a flow diagram for a process 600 for providing a wearable computing device in accordance with the present disclosure. In certain embodiments, the process 600 may be performed at least in part by a manufacturing system and/or control circuitry of the manufacturing system. For example, formation, implementation and provision of the wearable computing device and/or components thereof may be performed in one or more environments and by one or more devices and/or apparatuses of the manufacturing system when at least part of the process 600 is performed.

At block 602, the process 800 begins with providing an outer housing of the wearable computing device. In some implementations, process 800 includes formation of the outer housing, and/or retrieval of the outer housing. At block 604, the process 800 involves implementing an audio port by coupling it to the outer housing of the wearable computing device. In some embodiments the audio port is embedded in the outer housing of the wearable computing device. In some embodiments, the wearable computing device is an earbud, headphone, ear plug or any other similar device comprising an auditory speaker and designed to fit partially into an ear canal of a user.

At block 606, the process 600 involves implementing a light source configured to direct light into tissue (e.g., skin of ear canal) of a user wearing the wearable computing device, on an outer surface of the audio port. In some implementations, the outer surface of the audio port is substantially perpendicular to a direction in which sound from the audio port is projected.

At block 608, the process 600 includes implementing a light detector on the outer surface of the audio port a distance away from the light source, the light detector configured to detect light from the light source that reflects back from the user. In certain embodiments, implementing a light detector on the outer surface of the audio port a distance away from the light source includes providing an angle between the light source and the light detector such that an amount of light emitted by the light source travels a threshold distance in the tissue of the user and an amount of light detected by the light detector meets a threshold percentage of the amount of light emitted by the light source.

At block 610, the process 600 involves implementing a light-blocking portion between the light source and the light detector. Implementing the light-blocking portion may include providing a light-blocking rib extending in a radial direction from an outer surface of the audio port to the optically transparent portion of the audio tip. In some implementations, implementing the light-blocking portion includes providing a light source window to facilitate emission of light and providing a light detector window to facilitate detection of light.

In some implementations, the process 600 includes implementing a light detector on the outer surface of the audio port a distance away from the light source, the light detector configured to detect light from the light source that reflects back from the user. In some implementations, process 600 includes implementing a light detector on the outer surface of the audio port a distance away from the light source, the light detector configured to detect light from the light source that reflects back from the user.

Process 600 may further include coupling an audio tip to the audio port, the audio tip comprising an optically transparent portion and comprising the light-blocking portion implemented between the light source and the light detector.

Other Considerations

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

According to some embodiments, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices, wearable devices, or any other device that incorporates hard-wired and/or program logic to implement the techniques.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, ASICs, FPGAs, or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features or elements from one embodiment may be combined with other embodiments without departing from the teachings of this disclosure.

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Certain methods and/or processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium including a non-transitory computer-readable storage medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

Embodiments of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

Reference throughout this specification to "certain embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s).

Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A wearable computing device comprising:
one or more processors;
memory;
a physiological metric sensor system, including:
a light source configured to direct light into tissue of a user wearing the wearable computing device;
a light detector implemented a distance away from the light source and configured to detect light from the light source that reflects back from the user, the light source and light detector angled away from each other relative to a center of a light-blocking portion implemented between the light source and the light detector;
an audio port configured to be directed towards an ear canal of the user; and
control circuitry configured to:
activate the light source during a period of time; and
generate a light detector signal indicating an amount of light detected by the light detector during the period of time.

2. The wearable computing device of claim 1 further comprising one or more light field management features configured to steer or direct light from the light source to the light detector.

3. The wearable computing device of claim 2 wherein the one or more light field management features include at least one of a prism, light pipe, total internal reflection mirror, metallized mirror and a diffractive optical element.

4. The wearable computing device of claim 1 wherein the physiological metric sensor system is physically coupled to the audio port.

5. The wearable computing device of claim 1 wherein the physiological metric sensor system includes a photoplethysmographic (PPG) sensor, the PPG sensor including the light source and the light detector.

6. The wearable computing device of claim 1 wherein the light source is a light-emitting diode (LED) and the light detector is a photodiode.

7. The wearable computing device of claim 1 wherein the light source and the light detector are implemented on an outer surface of the audio port, the outer surface substantially perpendicular to a direction in which sound from the audio port is projected.

8. The wearable computing device of claim 1 wherein the light source and the light detector are implemented on an outer surface of the audio port, to provide that a configuration of the audio port in the ear canal of the user to optimize sound quality corresponds to a configuration of the light source and light detector to optimize light field management.

9. The wearable computing device of claim 1 further comprising an audio tip coupled to the audio port, the audio tip comprising an optically transparent portion and comprising the light-blocking portion implemented between the light source and the light detector.

10. The wearable computing device of claim 9 wherein the audio tip has a first size of a set of sizes.

11. The wearable computing device of claim 9 wherein the light-blocking portion is opaque.

12. The wearable computing device of claim 9 wherein the audio tip is made of silicone gel.

13. The wearable computing device of claim 9 wherein the light-blocking portion includes a light-blocking rib extending in a radial direction from an axis of the audio port to the optically transparent portion of the audio tip.

14. The wearable computing device of claim 9 wherein the light-blocking portion has a light source window to facilitate emission of light and a light detector window to facilitate detection of light.

15. The wearable computing device of claim 1 wherein the distance away from the light source corresponds to an angle between the light source and the light detector such that the amount of light travels a threshold distance in the tissue of the user and the amount of light meets a threshold percentage of light generated by the light source.

16. The wearable computing device of claim 1 wherein the audio port is communicatively coupled to an audio source.

17. The wearable computing device of claim 1 wherein the control circuitry is further configured to determine a physiological metric value based on the light detector signal.

18. A method for a wearable electronic device, comprising:

directing light, from a light source of the wearable electronic device, into tissue of a wearer of the wearable electronic device, the wearable electronic device including a light-blocking portion positioned between the light source and a light detector, and the light source and light detector positioned at an angle away from each other relative to a center of the light-blocking portion positioned between the light source and the light detector;

activating the light source for a period of time;

detecting, by the light detector, light which is reflected from the wearer for the period of time;

generating a light detector signal indicating an amount of the light detected by the light detector during the period of time; and providing, via an audio port of the wearable electronic device, physiological monitoring information based at least in part on the light detector signal.

19. The method for a wearable electronic device of claim 18, wherein a photoplethysmographic (PPG) sensor includes the light source and the light detector.

20. The method for a wearable electronic device of claim 18, wherein the light source and the light detector are implemented on an outer surface of the audio port.

* * * * *